United States Patent
Nakamura et al.

(10) Patent No.: US 10,202,215 B2
(45) Date of Patent: Feb. 12, 2019

(54) METHOD FOR PACKAGING MEDICAL SUPPLIES

(71) Applicant: Mani, Inc., Tochigi (JP)

(72) Inventors: Mitsunori Nakamura, Utsunomiya (JP); Masahiko Saito, Utsunomiya (JP)

(73) Assignee: MANI, INC., Utsunomiya-shi (JP)

(*) Notice: Subject to any disclaimer, the term of this patent is extended or adjusted under 35 U.S.C. 154(b) by 458 days.

(21) Appl. No.: 15/181,546

(22) Filed: Jun. 14, 2016

(65) Prior Publication Data

US 2016/0311567 A1   Oct. 27, 2016

Related U.S. Application Data

(63) Continuation of application No. 13/388,259, filed as application No. PCT/JP2010/062569 on Jul. 27, 2010, now abandoned.

(30) Foreign Application Priority Data

Jul. 31, 2009   (JP) .................... 2009-179143

(51) Int. Cl.
  *B65B 55/18*   (2006.01)
  *A61L 2/26*   (2006.01)
  (Continued)

(52) U.S. Cl.
  CPC ............ *B65B 55/18* (2013.01); *A61L 2/26* (2013.01); *B01D 53/228* (2013.01); *B65B 7/02* (2013.01);
  (Continued)

(58) Field of Classification Search
  CPC ... B65B 55/18; B65B 7/02; A61L 2/26; A61L 2202/181; A61L 2/206; A61L 2/00;
  (Continued)

(56) References Cited

U.S. PATENT DOCUMENTS

| | | |
|---|---|---|
| 3,552,638 A | 1/1971 | Quackenbush |
| 3,625,351 A | 12/1971 | Eisenberg |
| | (Continued) | |

FOREIGN PATENT DOCUMENTS

| | | |
|---|---|---|
| EP | 1520795 A1 | 4/2005 |
| JP | H0582221 A | 4/1993 |
| | (Continued) | |

OTHER PUBLICATIONS

Extended European Search Report for EP10804386.0 dated Aug. 30, 2013.

(Continued)

*Primary Examiner* — David J Walczak
(74) *Attorney, Agent, or Firm* — Isshiki International Law Office; Joseph P. Farrar, Esq.

(57) ABSTRACT

A method of packaging medical supplies includes overlapping a front film onto a back film, at least one of the front and back film being transparent and bacteria impermeable and does not transmit molecules as large as or larger than O2, extending a material that is gas permeable and bacteria impermeable along an opening side of at least one of the front and back film, and sealing the periphery of the front and back films except for the opening to form a packaging bag; inserting medical supplies in the packaging bag and then sealing the bag; sterilizing an interior of the packaging bag with EO gas injected through the material that is gas permeable and bacteria impermeable, removing the gas after sterilization and drying; and sealing the packaging bag so that the material that is gas permeable and bacteria impermeable does not communicate with the inside of the packaging bag.

2 Claims, 3 Drawing Sheets

(51) Int. Cl.
*B01D 53/22* (2006.01)
*A61B 50/30* (2016.01)
*B65B 7/02* (2006.01)
*A61L 2/20* (2006.01)

(52) U.S. Cl.
CPC ... *A61B 2050/314* (2016.02); *A61B 2050/316* (2016.02); *A61L 2/206* (2013.01); *A61L 2202/181* (2013.01)

(58) Field of Classification Search
CPC ............ B01D 53/228; A61B 2050/314; A61B 2050/316; A61B 2019/0267; A61B 2019/0268; A61B 2019/0286; A61B 19/026; B65D 75/30; B65D 33/04
See application file for complete search history.

(56) References Cited

U.S. PATENT DOCUMENTS

| | | |
|---|---|---|
| 3,939,971 A | 2/1976 | Tulis |
| 4,168,779 A | 9/1979 | Yokokoji et al. |
| 4,270,658 A | 6/1981 | Schuster |
| 4,318,506 A | 3/1982 | Hirsch |
| 4,630,729 A | 12/1986 | Hirt et al. |
| 4,660,721 A | 4/1987 | Mykleby |
| 4,730,726 A | 3/1988 | Holzwarth |
| 4,781,297 A | 11/1988 | Abrahamsson et al. |
| 5,049,624 A | 9/1991 | Adams et al. |
| 5,459,978 A | 10/1995 | Weiss et al. |
| 5,620,656 A | 4/1997 | Wensky et al. |
| 5,715,943 A | 2/1998 | Thompson, Jr. |
| 6,251,489 B1 | 6/2001 | Weiss et al. |
| 6,382,418 B1 | 5/2002 | Weder |
| 6,705,061 B1 | 3/2004 | Porret et al. |
| 6,767,509 B1 | 7/2004 | Griesbach et al. |
| 2004/0081601 A1 | 4/2004 | Morrissey et al. |
| 2004/0217035 A1 | 11/2004 | Tanaka |
| 2005/0067312 A1 | 3/2005 | Gupta et al. |
| 2005/0092636 A1 | 5/2005 | Su-Syin |
| 2005/0241981 A1 | 11/2005 | Gupta et al. |
| 2007/0092398 A1 | 4/2007 | McDonald |
| 2009/0200198 A1 | 8/2009 | Guelzow et al. |
| 2012/0205269 A1 | 8/2012 | Ludvig |
| 2014/0133785 A1 | 5/2014 | Diviesti et al. |
| 2014/0193299 A1 | 7/2014 | Leamy et al. |

FOREIGN PATENT DOCUMENTS

| | | |
|---|---|---|
| JP | 2001219976 A | 8/2001 |
| JP | 2002347781 A | 12/2002 |
| JP | 2005132491 A | 5/2005 |
| JP | 2007075368 A | 3/2007 |
| WO | 2005073091 A2 | 8/2005 |

OTHER PUBLICATIONS

International Preliminary Report for PCT/JP2010/062569 dated Feb. 7, 2012.
International Search Report directed to International Patent Application No. PCT/JP2010/062569, 8 pages including English translation.
Written Opinion for PCT/JP2010/062569 dated Nov. 9, 2010.

METHOD FOR PACKAGING MEDICAL SUPPLIES

CROSS-REFERENCE TO RELATED APPLICATION

This application is a continuation under 35 U.S.C. § 120 of prior U.S. application Ser. No. 13/388,259, filed on Jan. 31, 2012, which is a National Stage entry under 35 U.S.C. 371(c) of International Application No. PCT/JP2010/062569, filed on Jul. 27, 2010, which in turns claims priority to Japanese Application No. 2009-179143, filed on Jul. 31, 2009, the entire disclosures of which are incorporated herein by reference.

BACKGROUND

The present invention relates to a method for packaging medical supplies.

Background Art

The medical supplies such as surgical suture thread and suture needles are contained in a packaging bag after production, and are sterilized and then stored. When using, the packaging bag is opened and the medical supplies are taken out and then used.

The medical supplies are manufactured and contained in a packaging bag until use, which is not a constant period but storage is often a long time as well. Therefore, the sterilized state needs to be maintained throughout the storage period. A bacteria impermeable film is used for the packaging bag for this purpose.

Moreover, disinfection is conducted using sodium hypochlorite, hydrogen peroxide, and the like in hospitals, and these disinfectants may penetrate into the packaging bag. Since the packaging bag uses a bacteria impermeable film, introduction of a disinfectant is not required. Rather, it is preferable that the disinfectants do not penetrate into the packaging bag. This is because since these disinfectants have a bleaching action and the medical supplies are colored for identification, the colored medical supplies would be bleached.

Patent Document 1 (JP H05-82221B) is well-known as a conventional packaging bag containing medical supplies. This has a double bag structure.

FIGS. 3A-3C illustrate the packaging bag for medical supplies disclosed in Patent Document 1, where FIG. 3A is a top view, FIG. 3B is a cross section of FIG. 3A, and FIG. 3C is a top view illustrating a state without unnecessary parts. As shown in these drawings, medical supplies 1 are contained in an inner bag 2, and the inner bag 2 is contained in an outer bag 6, thereby constituting a double bag structure.

The medical supplies 1 in Patent Document 1 include surgical suture thread, staples, sponges, pins, prosthetic skin, or the like, and are hydrolyzable or able to enter the body and breakdown by moisture.

The inner bag 2 uses a heat-sealable plastic film 3, which is gas and bacteria impermeable, and a film 4, which is gas permeable and bacteria impermeable. The periphery of the films 3 and 4 is heat sealed except for an opening thereof, thereby forming a seal part 5a. The medical supplies 1 are contained in such an inner bag 2, the opening is heat sealed to form a seal part 5b, and then sealed.

This inner bag 2 is then placed inside the outer bag 6. The outer bag 6 is consisted of a film resulting from coating metal foil such as aluminum with heat-sealing resin, or laminating a resin film on metal foil such as aluminum. One of openings of the outer bag 6 is provided with a gas permeable and bacteria impermeable film 7. The periphery of the outer bag 6 is heat sealed except for an opening thereof, thereby forming a seal part 8a. The inner bag 2 is placed in the outer bag 6 and the opening is heat sealed to form a seal part 8b. FIGS. 3A and 3B illustrate this state.

The sterilization method of the medical supplies 1 is as follows.

A sterilizing gas such as ethylene oxide gas (EO gas) or the like is supplied to the entire outer bag 6. The sterilizing gas enters into the outer bag 6 via the film 7, sterilizing the inner surface of the outer bag 6 and the outer surface of the inner bag 2. The sterilizing gas also enters into the inner bag 2 via the gas permeable film 4, sterilizing the stored medical supplies and the inner surface of the inner bag 2.

After this, the double bag is placed in a vacuum device, degasification is performed, the sterilizing gas is discharged, and it is dried by a drying furnace, thereby removing the sterilizing gas and moisture from the outer bag 6 and the inner bag 2. Heat sealing is conducted at a position slightly deviant from the film 7 of the outer bag 6, and as shown in FIG. 3C, a seal part 8c is formed and the film 7 portion is cut off, thereby completing the process.

However, since the packaging bag shown in FIGS. 3A-3C is made of a film of metal foil such as aluminum laminated on both front and back surfaces of the outer bag 6, the inside cannot be seen. Therefore, what the stored medical supplies are cannot be visually confirmed.

While both the inner bag 2 and the outer bag 6 need only to be transparent synthetic resin films in order to be able to see inside, normally, such a film transmits not only O2, but sodium hypochlorite (NaClO) and hydrogen peroxide (H2O2) for sterilization as well.

In the case where the medical supplies 1 is suture thread, colored suture thread is normally used in order to display type, thickness, and the like of the suture thread. However, NaClO and H2O2 have disinfecting power and bleaching power, and when they penetrate into the inner bag, the color of the suture thread is bleached, whereby making the type of the suture thread indiscernible. Moreover, the suture thread is weakened by the bleaching chemical action.

The present disclosure, in light of the current condition, aims to provide a packaging bag, which allows visual confirmation of the content yet does not bleach medical supplies contained therein, a packaging bag containing medical supplies, and a packaging method for medical supplies.

A method of packaging medical supplies according to the present disclosure comprises the steps of overlapping a front film onto a back film, at least one of the front film and the back film being transparent and bacteria impermeable and does not transmit molecules as large as or larger than O2, extending a material that is gas permeable and bacteria impermeable along an opening side of at least one of the front film and the back film, and sealing the periphery of the front film and the back film except for the opening to form a packaging bag; inserting medical supplies in the packaging bag and then sealing the opening side; sterilizing an interior of the packaging bag with EO gas injected through the material that is gas permeable and bacteria impermeable, removing the gas after sterilization using a vacuum device or by exchanging the gas with another gas, and drying by dry heat or air drying; and sealing the packaging bag so that the material that is gas permeable and bacteria impermeable does not communicate with the inside of the packaging bag.

Preferably, the transparent film that is bacterial impermeable and does not transmit molecules as large as or larger than O2 is a plastic film coated with silica or alumina According to the present invention, even if the packaging bag is exposed to H2O2 or sodium hypochlorite for disinfection after medical supplies are sealed therein, the H2O2 or sodium hypochlorite will not enter the packaging bag and may thereby prevent bleaching of the medical supplies. Moreover, since the films are transparent, content may be confirmed from the outside, which is an excellent result.

BRIEF DESCRIPTION OF DRAWINGS

FIG. 1A is a top view of a packaging bag for medical supplies according to the present invention, FIG. 1B is a central cross section of FIG. 1A, and FIG. 1C is a top view of a state where medical supplies are contained in the packaging bag for medical supplies according to the present invention and sealed therein;

FIG. 3A is a top view, FIG. 3B is a cross section of FIG. 3A, and FIG. 3C is a top view illustrating a state without unnecessary parts.

DETAILED DESCRIPTION

Embodiments according to the present invention are described with reference to accompanying drawings forthwith.

Figure 1A:
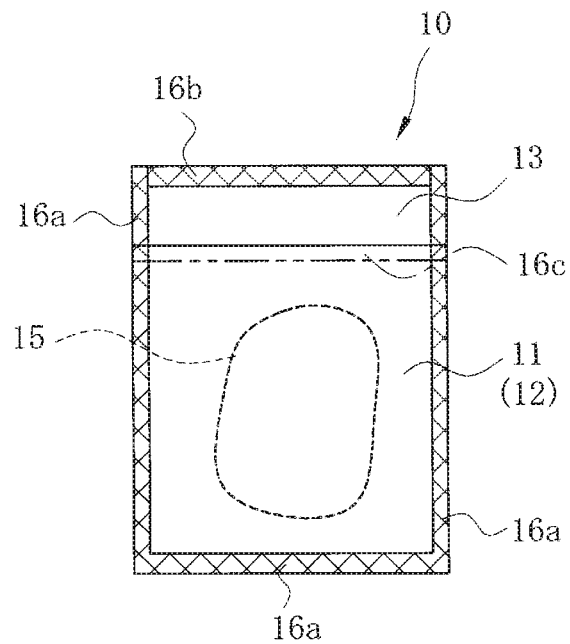
FIGS. 1A-1C illustrate a working example of the present invention, where
Figure 1B:
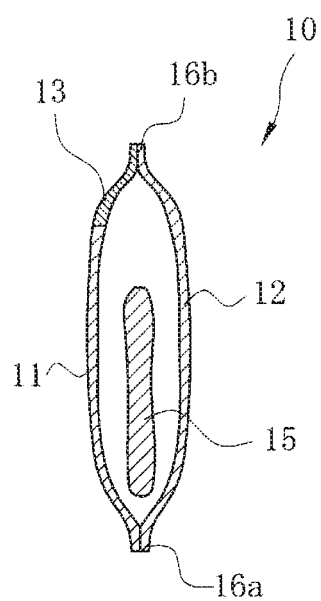
Figure 1C:
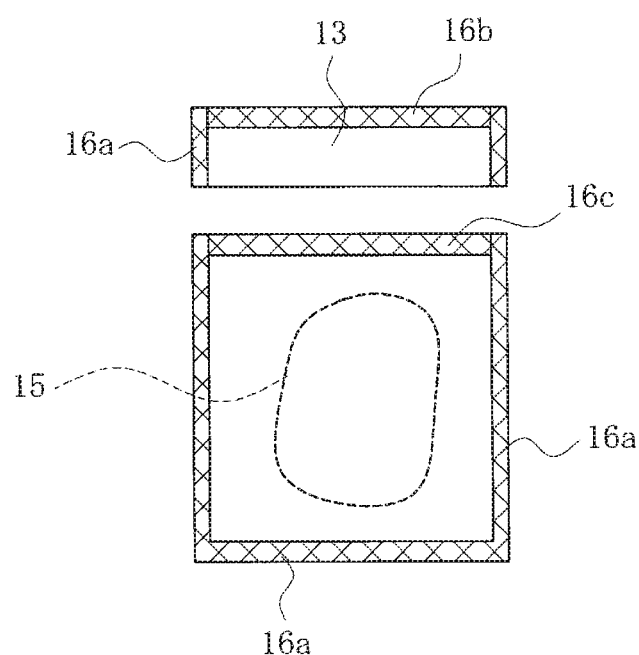

FIGS. 1A-1C illustrate a working example of the present invention, where FIG. 1A is a top view of a packaging bag for medical supplies according to the present invention, FIG. 1B is a central cross section of FIG. 1A, and FIG. 1C is a top view of a state where medical supplies are contained in the packaging bag for medical supplies according to the present invention and sealed therein.

In general, various synthetic resin films such as PET, polypropylene, and nylon are gas permeable, and have a property of transmitting O2, of course, as well as hydrogen peroxide, sodium hypochlorite, and the like. The inventors of the present invention have found that deposition of silica and alumina on various synthetic resin films such as PET, polypropylene, and nylon allows achievement of a characteristic of not transmitting hydrogen peroxide and sodium hypochlorite while transmitting oxygen marginally, whereby this knowledge has lead to the completion of the present invention. Deposition methods for silica and alumina utilize PVD and CVD.

Note that whether the film on which silica and alumina are deposited allows transmission can be thought to depend on the magnitude of the molecular weight thereof. Namely, the molecular weight of oxygen is 32, the molecular weight of hydrogen peroxide is 34, and the molecular weight of sodium hypochlorite is 74, and the film transmits those with smaller molecular weights than 32, where hydrogen peroxide and sodium hypochlorite with molecular weights greater than 32 are not transmitted as they are greater than the molecular weight of oxygen.

While it has been said that the film does not transmit oxygen, hydrogen peroxide, and sodium hypochlorite, this is not meant in the strictest sense. Oxygen may be marginally transmitted, and hydrogen peroxide and sodium hypochlorite are only more difficult to be transmitted than oxygen, which does not mean that they are not transmitted through at all. However, since quantities of transmitting hydrogen peroxide and sodium hypochlorite are extremely minute, they are negligible. According to the inventors' experiment, favorable results were found when oxygen transmittance is 0.11 (cm3/m2 day·atm) or less under a condition of 23 degrees Celsius and 65% RH. Description of this experiment will be given as a working example.

As shown in FIGS. 1A and 1B, a packaging bag 10 for medical supplies according to the present invention has a front side film 11 and a backside film 12. Both the front side film 11 and the backside film 12 are various synthetic resin films such as polypropylene or nylon on which silica and alumina are deposited, maintaining a transparent state.

In the working example of FIGS. 1A-1C, the front side film 11 and the backside film 12 are both transparent and utilize the same material, but are not limited thereto. A transparent film on which silica or alumina is deposited should be used on at least one side. For example, either the front side film 11 or the backside film 12 may be a film made by laminating or coating a heat-sealing resin on metal foil such as aluminum.

A film 13 made of a gas permeable, bacteria impermeable material is extended along an opening side (upper end in the drawing) of the front side film 11. These films 11 to 13 are heat sealable, and left, right, and lower portions are heat sealed so as to form a seal part 16a, thereby forming a bag shape. Alternatively, one sheet may be folded over at the central portion and sealed on two sides so as to form a bag shape. The medical supplies 15 are contained in this packaging bag 10, and the upper opening in the drawing is heat sealed to form a seal part 16b. When the seal part 16b is formed by folding one sheet, three sides are sealed. The medical supplies 15 are not particularly limited as long as they are for medical use. The medical supplies 15 are contained in a packaging bag in the above description, and sterilization processing will be executed next.

The sterilization processing is as follows.

A sterilizing gas such as EO gas (ethylene oxide gas) or the like is supplied to the entire packaging bag 10. The sterilizing gas enters into the packaging bag 10 via the film 13, which is at the opening rim of the packaging bag 10, sterilizing the inner and outer surfaces of the packaging bag 10 and the contained medical supplies 15.

After this, the packaging bag 10 is placed in a vacuum device, degasification is performed, the sterilizing gas is discharged, and it is dried by a drying furnace, thereby removing the sterilizing gas from the packaging bag 10. The sterilizing gas removal method, aside from the above method, may also be a method of exchanging it with another gas such as air, or a method of adding dry heat so as to dry it. Dry-heat sterilization is a sterilization method of thermal denaturalization and devitalization of microorganisms, enzymes, and proteins by heating at 160 to 200 degrees Celcius for 30 minutes to 2 hours. Once the sterilizing gas is removed, the films 11 and 12 are heat sealed at a position where the film 13 of the packaging bag 10 does not communicate with the inside of the packaging bag 10, thereby forming a seal part 16c as shown in FIG. 1C, and the film 13 portion is then cut off, completing the process. If the seal portion 16c is formed, cutting off the film 13 portion may be omitted.

If the packaging bag in this state is stored at a hospital or the like, even if disinfection is carried out at the hospital using hydrogen peroxide and sodium hypochlorite, hydrogen peroxide and sodium hypochlorite no longer enters the packaging bag 10, thereby allowing prevention of trouble such as suture thread being decolorized.

Figure 2:
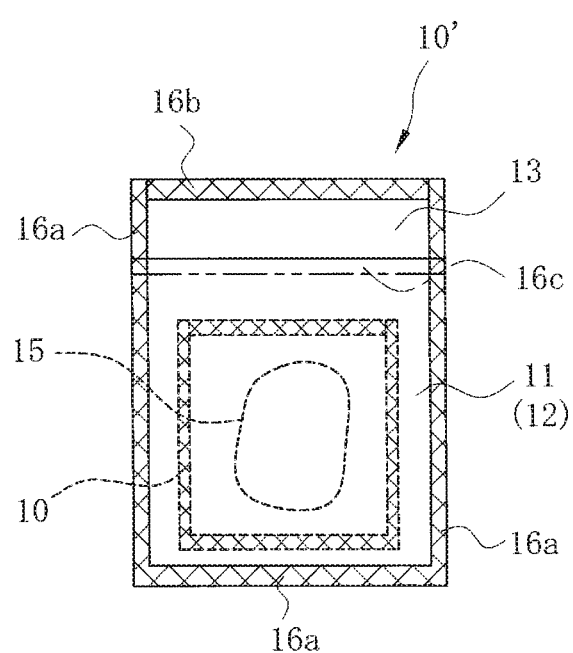
FIG. 2 illustrates a working example of the present invention.
Figure 3A:
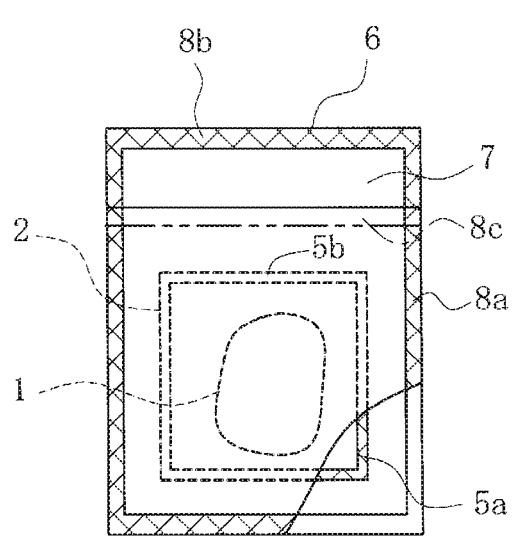
FIGS. 3A-3C illustrate a conventional packaging bag for medical supplies, where
Figure 3B:
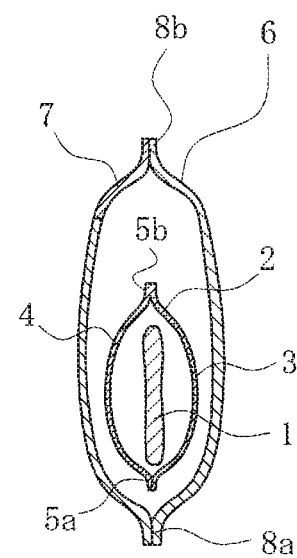
Figure 3C:
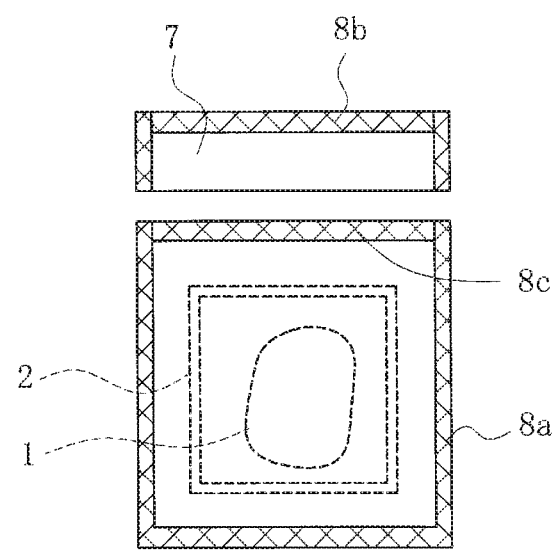

FIG. 2 is a working example where the packaging bag 10 containing the medical supplies 15 shown in FIGS. 1A-1C is contained in a larger, outer packaging bag 10' having the same constitution as the packaging bag 10. The packaging bag 10' has the same structure as the packaging bag 10. An opening of the outer packaging bag 10' containing the inner packaging bag 10 is heat sealed so as to form the seal part 16b, sterilization processing is executed in the same manner as for the packaging bag 10, and the seal part 16c is formed, thereby allowing the same double bag structure as in Patent Document 1. In this case, since the films 11 and 12 result from silica and alumina deposited on transparent plastic films, transparency is assured, allowing easy confirmation of the medical supplies contained therein. Moreover, by making the film on the same side as the packaging bag 10 and the packaging bag 10' be transparent in the case where one of the films 11 and 12 is a laminated film of metal foil such as aluminum or the like, the content may be visually confirmed even if it is a double bag structure.

While the packaging bag 10 and the packaging bag 10' have the same structure, this same structure referred to here means functionally the same structure, and the packaging bag 10 and the packaging bag 10' are not limited to being made of the same material.

The packaging bag 10 of the present invention produces improvements, such that contents may be visually confirmed if the films are PET coated with silica, chlorine gas is not generated even if it is burned after disposal, there is hardly any residue after burning, and it may be lighter than a film using aluminum foil.

Note that a transparent film that does not transmit any oxygen may be manufactured depending on type of plastic, deposition method of silica and alumina, and the like. If a film that does not transmit oxygen is used, the bag may be used for packaging hydrolyzable medical supplies.

WORKING EXAMPLE 1

Table 1 shows results from an experiment using four types of packaging bags A, B, C, and D. In Table 1, thickness (μm) is thicknesses of the films 11 and 12 constituting the packaging bag 10 for medical supplies, where 50+80 denotes that thickness of the film 11 is 50 micrometers and that of the other film 12 is 80 micrometers. Both of these films have used a film on which silica is deposited on each side.

TABLE 1

| Sample | Thickness (μm) | Oxygen transmission (cm3/m2day) | 7 days later Change in color | Strength | 14 days later Change in color | Strength |
|---|---|---|---|---|---|---|
| A | 80 + 80 | 0.06 | ⊚ | 44.7 | ⊚ | 45.3 |
| B | 50 + 80 | 0.09 | ⊚ | 44.2 | Δ | 40.8 |
| C | 80 + 80 | 0.13 | Δ | 39.5 | X | 19.7 |
| D | 50 + 80 | 0.20 | X | 33.8 | X | 16.1 |
| Control | — | — | ⊚ | 44.1 | ⊚ | 44.1 |

⊚ No decolorization
Δ Slight decolorization
X Decolorization

Oxygen transmittance (unit is cm3/m2·day·atm) is transmission between inside and outside the packaging bag 10. Oxygen transmittance of both the film 11 and the film 12 is in a combined state.

Change in color means that whether or not decolorization has occurred has been visually determined from change in color of the suture thread stored in the packaging bag 10.

The packaging bags 10 of the types A, B, C, and D contain the same suture thread, and each of the packaging bags 10 was kept in a state exposed to hydrogen peroxide in a plastic container. Tensile strength and decolorization were determined after seven days and fourteen days.

A control had been prepared for comparative purposes and had the suture thread contained in the packaging bags 10 of the types A, B, C, and D, but was not exposed to hydrogen peroxide.

Validity is investigated through comparison with the control, which has ideal quality having sufficient tensile strength without any change in color, as a reference for the experiment results.

After seven days, A and B exhibited no decolorization, which is the same result as with the control, C had slight decolorization, and D had greater decolorization. Tensile strengths for A to D were 44.7 gf, 44.2 gf, 39.5 gf, and 33.8 gf, respectively, A and B had 100% tensile strength against the control, and C and D had 90% and 77%, respectively.

After fourteen days, A exhibited no decolorization, which is the same result as with the control, B had slight decolorization, and C and D were completely decolorized. Tensile strengths for A to D were 45.3 gf, 40.8 gf, 19.7 gf, and 16.1 gf, respectively, and they had 100%, 93%, 45%, and 37% tensile strength against the control, respectively.

The above results are found to be proportional to oxygen transmittance through examination by the inventors. To summarize the above results, A (0.06 oxygen transmittance) attained the same results as the control, and is considered a favorable film having ideal quality. B (0.09 oxygen transmittance) had slight decolorization and the tensile strength was favorable, and is thereby acceptable. C (0.13 oxygen transmittance) and D (0.20 oxygen transmittance) had complete decolorization as well as remaining strength was half or less than the control after fourteen days, and are thereby unusable. It is understood therefrom that there is no problem in use as long as the film had an oxygen transmittance of at least 0.09. Moreover, favorable use may be expected as long as the film has an oxygen transmittance of approximately 0.11, with consideration of a possible error of 0.09.

Note that while silica-coated films have been used in the above working examples, the case of alumina coating may also be treated the same as the silica-coated film by setting the upper limit of oxygen transmittance to approximately 0.11.

DESCRIPTION OF REFERENCE NUMERALS

10: Packaging bag for medical supplies
11: film (bacteria impermeable and does not transmit molecules of O2 or larger)
12: film (bacteria impermeable and does not transmit molecules of O2 or larger)
13: (gas permeable and bacteria impermeable) film
15: Medical supplies
16a: Seal part
16b: Seal part
16c: Seal part

The invention claimed is:
1. A method of packaging medical supplies, comprising the steps of:
overlapping a front film onto a back film, at least one of the front film and the back film being transparent and bacteria impermeable and does not transmit molecules as large as or larger than $O_2$, extending a material that is gas permeable and bacteria impermeable along an opening side of at least one of the front film and the back film, and sealing the periphery of the front film and the back film except for the opening side to form a packaging bag;

inserting medical supplies in the packaging bag and then sealing the opening side;

sterilizing an interior of the packaging bag with EO gas injected through the material that is gas permeable and bacteria impermeable, removing the gas after sterilization using a vacuum device or by exchanging the gas with another gas, and drying by dry heat or air drying; and sealing the packaging bag so that the material that is gas permeable and bacteria impermeable does not communicate with the inside of the packaging bag.

2. The method of packaging medical supplies of claim 1, wherein the transparent film that is bacterial impermeable and does not transmit molecules as large as or greater than $O_2$ is a plastic film coated with silica or alumina.

* * * * *